United States Patent [19]

Kato et al.

[11] Patent Number: 4,529,552
[45] Date of Patent: Jul. 16, 1985

[54] COMPOSITE OXYALKOXIDES AND DERIVATIVES THEREOF

[75] Inventors: Iwao Kato; Yoshihiko Nakamura; Tetsuo Yoshimoto, all of Kanagawa; Masanori Iwamori, Chiba; Kazuo Ozawa, Chiba; Makoto Asai, Chiba, all of Japan

[73] Assignee: Nippon Soda Company Limited, Tokyo, Japan

[21] Appl. No.: 463,880

[22] PCT Filed: May 25, 1982

[86] PCT No.: PCT/JP82/00190

§ 371 Date: Jan. 24, 1983

§ 102(e) Date: Jan. 24, 1983

[87] PCT Pub. No.: WO82/04254

PCT Pub. Date: Dec. 9, 1982

[30] Foreign Application Priority Data

May 25, 1981 [JP] Japan ................................ 56-78882

[51] Int. Cl.$^3$ .............................................. C07F 7/28
[52] U.S. Cl. ........................................ 556/40; 556/54; 556/55; 556/56
[58] Field of Search ...................................... 260/429.5

[56] References Cited

U.S. PATENT DOCUMENTS

| | | | |
|---|---|---|---|
| 2,720,502 | 10/1955 | Caldwell | 260/429.5 X |
| 2,758,911 | 8/1956 | Lynd et al. | 260/429.5 X |
| 2,789,969 | 4/1957 | Reynolds et al. | 260/429.5 X |
| 2,827,360 | 3/1958 | Blumenthal | 260/429.5 X |
| 3,006,941 | 10/1961 | Mudrak et al. | 260/429.5 X |
| 3,017,282 | 1/1962 | Brill | 260/429.5 X |
| 3,157,661 | 11/1964 | Gray | 260/429.5 X |
| 3,231,328 | 1/1966 | Pechini | 260/429.5 X |
| 3,647,364 | 3/1972 | Mazdiyasni | 260/429.5 X |
| 3,699,137 | 10/1972 | Termin et al. | 260/429.5 |
| 3,721,689 | 3/1973 | Bardinet | 260/429.5 |
| 4,056,588 | 11/1977 | Baniel et al. | 264/63 |
| 4,333,881 | 6/1982 | Greco et al. | 260/429.5 X |

FOREIGN PATENT DOCUMENTS 1109372 4/1968 United Kingdom .

OTHER PUBLICATIONS

Flaschen, JACS, 77, 6194 (1954).
Chemical Abstracts, 55, 23312f, g (1961).

*Primary Examiner*—Helen M. S. Sneed
*Attorney, Agent, or Firm*—George B. Oujevolk

[57] ABSTRACT

Composite oxyalkoxides and their derivatives are novel organometallic compounds which give alkaline earth metal titanates such as barium titanate or strontium titanate by hydrolysis or thermal decomposition. The oxyalkoxides are synthesized by the reaction between an alkoxytitanium and an alkaline earth metal hydroxide, and their derivatives are synthesized by the reaction between the composite oxyalkoxide and a chelating agent.

8 Claims, 6 Drawing Figures

COMPOSITE OXYALKOXIDES AND DERIVATIVES THEREOF

THE FIELD OF THE INVENTION

The present invention relates to an organo-metal compound and more particularly, it relates to composite oxyalkoxides and their derivatives using as a raw material for manufacturing composite oxides.

BACKGROUND OF THE INVENTION

Composite oxides involving barium titanate and strontium titanate or the like have a peculiar dielectric nature, a piezo-electric nature, a mechanical feature and a chemical feature, so that those composite oxides are a very important materials. These oxides have hitherto been manufactured by carrying out the reaction in the solid phase at a high temperature. For example, a titanate salt of an alkaline earth metal has been manufactured by a reaction step of a titanium oxide with a carbonate salt of an alkaline earth metals at a high temperature. The said reaction step is represented by the following reaction formula:

$$TiO_2 + MCO_3 \rightarrow MTiO_3 + CO_2$$

(wherein M denotes an atom of an alkaline earth metal.) However, the composite oxides obtained by this process contain a comparatively large amount of impurity and further, as to reactants of the composition, for example, in the event of producing the titanate salt of alkaline earth metal, the reaction compound does not necessarily contain the stoichiometric amounts, even if the reaction is carried out with a definite condition by choosing a definite atomic ratio (Ti/M) of titanium (Ti) in proportion to the alkaline earth metal (M). Further, the composite oxides obtained have a granular diameter of several microns or more and a distribution of its granular diameter has a wider range. Consequently, the composite oxides obtained with this process can not be said to have a high efficient capacity as electronic raw material which requires a small size mechanical structure having the high capacity.

As a process for producing the composite oxides and improving the drawback of the solid phase reaction, a method for performing a chemical reaction in a solution (hereinafter, this is abbreviated as "the solution method") is proposed. Generally, the solution method has the following features.

(1) A purifying step by removing the impurity can be comparatively easily carried out and thereby, a high purity of the desired material is obtained.

(2) The desired material having a granular diameter of one milli-micron or less and a narrow distribution of granular size is obtained.

(3) An addition of a third material is easily carried out and even if a micro amount is added, a homogeneous composition can be obtained and consequently, the desired material having features conforming to the desired purpose can be obtained.

However, the process for producing the composite oxide with the conventional solution method involves various drawbacks, so that it can not be adopted as an industrial process of obtaining the composite oxide.

For example, in a process for producing a finely pulverized particles of barium titanate ($BaTiO_3$) by a reaction of an aqueous solution containing barium hydroxide [$Ba(OH_2)$] with titanium alkoxide [$Ti(OR)_4$] as disclosed in [J.A.C.S. 77 6194 (1954) and J.Amer.Ceram.-Soc. 49 291 (1966)], it is difficult to control the ratio of the titanium/barium (Ti/Ba) in the finished product as a stoichiometric value.

In one process for hydrolyzing an alcohol mixed solution of barium alkoxides [$Ba(OR)_2$] and titanium alkoxides [$Ti(OR)_4$] and producing barium titanate [$BaTiO_3$], as disclosed in the [U.S. Pat. No. 3,647,364] and in another process for producing strontium titanate by using strontium alkoxides [$Sr(OR)_2$] in the place of the barium alkoxides and the procedure disclosed in the [J.Amer.Ceram.Soc. 53 91 (1970)], the alkaline earth metal alkoxides used as the raw material are expensive and it is difficult to obtain the raw material. Therefore, these processes are not practical.

In the process for producing barium titanate [$BaTiO_3$] with a reaction of barium hydroxide [$Ba(OH)_2$] and titanium tetrachloride [$TiCl_4$] as disclosed in [U.S. Pat. No. 3,725,539] and in another process for producing barium titanate [$BaTiO_3$] by treating barium chloride [$BaCl_2$] and titanium tetrachloride [$TiCl_4$] with hydrogen peroxide [$H_2O_2$], as disclosed in Japanese Open Pat. No. 69599/1974, or in other words, in the process for producing barium titanate, by using a compound other than the titanium alkoxide, as a titanium source, it is difficult to control the ratio of titanium/barium as a stoichiometric quantity. Also, these reaction operations are complicated.

In a process for making barium titanate by the thermal decomposition of titanyl barium oxalate which is obtained by reacting with a mixed solution containing titanium ion and barium ion and oxalic acid, as disclosed in the [U.S. Pat. No. 2,758,911] the titanyl barium oxalate is thermally decomposed at a high temperature of 700° C. or more and consequently, a coarse grain of the crystal is produced. Furthermore, it is difficult to add a third material.

OBJECTS OF THE INVENTION

An object of the present invention is to provide a useful organo-metal compound, the composite oxyalkoxides and their derivatives.

Another object is to provide a process for producing said organo-metal compound and an improved process for producing the composite oxides by the solution method by using the said organo-metal compound.

The inventors carried out the present invention by eager research to achieve the aforementioned objects and as a result, they discovered a fact that the composite oxyalkoxides can be produced with a reaction of alkaline earth metal hydroxide and titanium alkoxides and further, a fine crystal of alkaline earth metal titanate having a stoichiometric ratio of titanium/barium can be easily obtained with a hydrolysis of the said composite oxyalkoxides.

DISCLOSURE OF THE INVENTION

The present invention comprises the production of composite oxyalkoxides which are represented by a composition formula [I], as a repeated constituent unit:

$$[MTiO_2(OR)_2] \qquad [I].$$

where its repeated number is in a range of 1 to 20 and the derivatives of the composite oxyalkoxides in which a substituent represented by [—OR] in the said composition formula [I] is partially or totally substituted with a chelating agent.

In the composition formula [I] by the present invention, M denotes an alkaline earth metal atom and for example, it denotes the same or different kinds of calcium, magnesium, barium and/or strontium. R denotes an alkyl group by straight chain form or branched chain form having 1 to 6 carbon atoms, i.e., a methyl group, ethyl group, propyl group, isopropyl group, butyl group tertiary-butyl group or hexyl group, substituted alkyl group by hydroxy group, alkoxy group having 1 to 3 carbon atom(s) or halogen, such as 1,4-butane diol residue, glycol residue or cellosolve residue, a substituted or unsubstituted cyclo-alkyl group involving cyclohexyl group or 1-methyl cyclopentyl group, an alkenyl group involving allyl group or crotyl group, and a substituted or unsubstituted aralkyl group such as benzyl group, phenyl ethyl group and furthermore R denotes the same or different kinds of aforementioned substitutent(s).

The composite oxyalkoxides of the present invention are examples of monomers of the compounds having a repeating constituent unit formulated as shown thereafter or oligomers of the compounds having repeating constituent unit in a range of 2 to 20.

$BaTiO_2[OCH(CH_3)_2]_2$, $SrTiO_2[OCH(CH_3)_2]_2$, $BaTiO_2[O(CH_2)_3CH_3]_2$,
$SrTiO_2[O(CH_2)_3CH_3]_2$, $BaTiO_2[O(C_6H_{10})-2-C_2H_5]_2$, $BaTiO_2(OCH_2.C_6H_5)_2$,
$BaTiO_2(OCH_2.CH_2OH)_2$,
$BaTiO_2(OCH_3)_a[OCH(CH_3)_2]_b$ where $a+b=2$,
$SrTiO_2(OCH_3)_a[OCH(CH_3)_2]_b$ where $a+b=2$ and
$Ba_xSr_yTiO_2[O(CH_2)_3CH_3]_2$ where $x+y=1$.

Another aspect of the present invention comprises composite oxyalkoxide derivatives where the substituent represented by [—OR] in the composite oxyalkoxides having the composition formula [I] as the repeating constituent unit is partially or totally substituted with a chelating agent having two kinds or more of intermolecular functional groups, for example, the chelating agent having a hydroxy group, amino group or carbonyl group such as β-diketones involving acetylacetone or benzoyl acetone and α- or β-ketonic acids involving acetoacetic acid, propionyl butyric acid, benzoyl acetic acid or acetyl formic acid, and α- or β-ketonic acid esters involving methyl, ethyl, propyl or butyl ester of the said ketonic acid, α- or β-oxy acid involving glycollic acid, lactic acid, α- or β-oxy acid esters involving methyl, ethyl, propyl, or butyl ester of the said oxy acid, α- or β-oxy ketones involving diacetone alcohol or acetoin, α- or β-oxy aldehydes involving glycollic aldedhyde or aldol, α-amino acids involving glycine or alanine and α- or β-amino alcohol such as aminoethylalcohol. Thus, the derivative of the composite oxyalkoxides having the same kinds or different kinds of foregoing specified chelating substituent is obtained.

Examples of the composite oxyalkoxide derivatives of the present invention are examplified below. It comprises monomers of the compounds having repeated constituent unit as denoted in the following composition formula or these oligomer having repeating constituent unit in a range of 2 to 20.

$BaTiO_2[OCH(CH_3)_2].(OCOCH_2COCH_3)$,
$SrTiO_2[O(CH_2)_3CH_3][(OCH_2CH_2)_2N(CH_2)_2OH]$,
$Ba_xSr_yTiO_2[OCH(CH_3)COO]$, where $x+y=1$.

These composite oxyalkoxides and their derivatives are soluble in organic solvents and a high concentration of the solution can be obtained depending on the kinds of the solvents used. Further, the titanate salt(s) of alkaline earth metal can be easily produced with a hydrolysis or a thermal decomposition of these solutions. Particularly, the former compound absorbs a moisture in the atmosphere and it is subject to the kind of the substituent denoted by [—OR] in the composition formula [I], whereas the latter type compound is almost stable in the usual state without being subjected to hydrolysis by the moisture in the atmosphere.

The organic solvent solution containing the composite oxyalkoxides and/or their derivatives by the present invention is treated with a direct hydrolysis or a thermal decomposition and thereby, a fine granular particles of the alkaline earth metal titanate salt is obtained. Further, the said organic solvent solution produces a film upon a thermal resistant base plate such as glass, ceramic or metal plate with a dipping process or a spraying process and by means of its thermal decomposition, the film of the alkaline earth metal titanate salt is obtained. Furthermore, a solvent soluble polymer is added to said organic solvent solution and a film moulding or a fiber molding is produced and then, by means of hydrolysis or thermal decomposition, an optional form of the alkaline earth metal titanate salt can be obtained.

The composite oxyalkoxides and their derivatives are synthesized in such manner that a titanium alkoxide having a general formula [II]

is made to react with an alkaline earth metal hydroxide having a general formula [III]

as denoted in the following reaction formula [1]

and thereby, the said composite oxyalkoxides is synthesized and then, the composite oxyalkoxides is made to react with a desirable chelating agent and thereby, the composite oxyalkoxide derivative is synthesized, where R and M have the same significance as heretofore defined and n is an integer. In the event of synthesizing the composite oxyalkoxide derivatives, the titanium alkoxide having the general formula [II] is made to react with the desirable chelating agent and then, the resulting reaction compound may be reacted with an alkaline earth metal hydroxide.

The titanium alkoxide having the general formula [II], as one of raw materials may be chosen from a titanium alkoxide containing the "R substituent" which corresponds with the purposed composite oxyalkoxides or derivatives. The titanium alkoxide involving tetramethoxy titanium, tetraisopropoxy titanium, tetrabutoxy titanium or diethoxy-diisopropoxy titanium is desirably used. Particularly, the tetraisopropoxy titanium and tetrabutoxy titanium which are industrially manufactured and easily obtained are desirably used.

The composite oxyalkoxides having a different kind of substituent [—OR] group is obtained in such manner that a composite oxyalkoxide is produced by using the lower alkoxy-titanium as a raw material and the composite oxyalkoxide is made to react with an alcohol having a desirable substituent [—OR] group and thereby, it is totally or partially substituted by introducing a desirable alkyl group.

As the alkaline earth metal hydroxide having the general formula [III] the anhydrous or dried salt may be used and said anhydrous or dried salt is desirably used for preventing the hydrolysis of the titanium alkoxide used and the composite oxyalkoxides produced.

The synthetic reaction of the composite oxyalkoxide in the reaction formula [1] proceeds in the presence of an organic solvent or in the absence thereof, but said synthetic reaction proceeds mildly in the presence of the organic solvent. Further, as the organic solvent, an organic solvent having a higher boiling point than that of liberated alcohol is desirably used, because the alcohol is liberated according to how the reaction proceeds and it must be exhausted to the outside of reaction system. The use of the organic solvent having a high polar nature stabilizes the titanium ion and retards a reaction velocity, so that it is undesirable. Further, in case the substituent [—OR] group in a substitution reaction is totally or partially substituted with another desirable subsutuent, an alcohols is desirably used as the said organic solvent.

The reaction denoted by the reaction formula [1] is carried out in the presence of an inert gas such as $N_2$ gas and argon gas or a vapour atmosphere generated from the alcohol or the solvent used and thereby, it is intended to prevent a hydrolysis reaction and an occurrence of a carbonate salt which is generated by intermingling carbon dioxide gas with the reactant. Its reaction temperature and its reaction time can be variable by the kinds of the raw materials and the employing organic solvent(s). Generally, the reaction temperature is chosen in a range of 50° C. to 300° C., preferably in a range of 100° C. to 250° C. and the reaction time is chosen in a range of 0.5 to 60 hour(s), preferably in a range of 1.0 to 15 hour(s). As a desirable mode, the reaction is carried out during 1.0 to 3.0 hour(s) by refluxing the organic solvent.

Any non-reacted raw material in a solid state and/or liquid state and impurities of the by-product and the reaction solvent in a reaction mixture, other than the composite oxyalkoxide can be separated by a conventional operation of separating a liquid component from a solid component such as a filtrating step and another conventional operation of gas-liquid separating such as a concentrating step and a distilling step and thereby the said composite oxyalkoxide, as the objective compound can be separated.

Generally, the said composite oxyalkoxide is a monomer or an oligomer which is represented by the composite formula [I] and has an average repeated number of the constituent unit in a range of 1 to 100 and it is variable depending on the kinds of the raw materials, its blending ratio, the solvent used, the kinds, the amount used, and the reaction condition such as reaction temperature and the reaction time and the post reaction treating conditions. An oligomer having the average repeating number of 4 to 12 is obtained under usual conditions. Further, by utilizing the variations of chemical properties and physical properties caused by the difference of the repeated unit number, a material having a narrow distribution of the repeating unit number can be produced.

Moreover, the composite oxyalkoxide may be obtained with the following process:

(a) The reaction which comprises making an alkoxy titanium to react with M-alkoxide in the presence of two multiple molar amount of water proportional to the said M-alkoxide where M denotes an alkaline earth metal.

(b) The reaction which comprises making M-oxide as a replaced reactant for the M-hydroxide to react with alkoxy titanium in the presence of an equal molar amount of water proportional to the M-oxide and the alkoxy titanium.

(c) The reaction which comprises making a reaction compound of the alkoxy titanium and the water [Ti-O(OR)$_2$] to react with the M-oxide.

On the other hand, the composite oxyalkoxide derivative is synthesized with a process which comprises adding a desirable chelating agent in a synthetic reaction solution containing the composite oxyalkoxide and completely finishing the reaction. Of course, it can be also synthesized with a process in which the composite oxyalkoxide, once separated is made to react with the chelating agent in an organic solvent. This synthetic reaction is carried out under air-tight conditions on the basis of the same reason which occurs in the synthetic reaction of producing the composite oxyalkoxide. Its reaction condition is variable depending on the kinds of the composite oxyalkoxides and the chelating agent, the presence or absence of the solvent used, the kinds and the amount, but generally, the reaction temperature is chosen in the range of 0° C. to 300° C., desirably is the range of 20° C. to 250° C. and the reaction time is chosen in the range of 0.5 to 10 hour(s), desirably in the range of 1.0 to 5.0 hour(s).

The composite oxyalkoxide derivative(s) obtained by the foregoing reaction is a monomer or an oligomer having an average repeating number of the standard constituent unit in the range of 1 to 100, even if the average repeating number depends on the repeating constituent unit number of the composite oxyalkoxide. Usually, the oligomer having the average repeating number of 4 to 12 is obtained under usual reaction condition.

Further, the distribution extent of the said constituent unit repeating number can be narrowed in a similar way that was carried out for the composite oxyalkoxides.

The invention will be better understood from the following graphic illustrations and examples, in which:

BRIEF DESCRIPTION OF THE DRAWINGS

The FIG. 1 to the FIG. 6 show one example of the infrared ray absorption curves of the composite oxyalkoxides and these derivatives.

FIG. 1: $BaTiO_2(OCH_3)_{1.8}[OCH(CH_3)_2]_{0.2}$,
FIG. 2: $SrTiO_2(OCH_3)_{1.9}[OCH(CH_3)_2]_{0.1}$,
FIG. 3: $BaTiO_2(OCH_2CH_2CH_3)_2$,
FIG. 4: $BaTiO_2(OCH_3)_{1.4}[OCH(CH_3)_2]_{0.6}$,
FIG. 5: $BaTiO_2[OCH(CH_3)_2](OCOCH_2COCH_3)$,
FIG. 6: $Ba_{0.5}Sr_{0.5}TiO_2[OCH(CH_3)COO]$.

THE BEST MODES FOR PERFORMING THE INVENTION

The invention is carried out in accordance with the following general formula where the letters "n", "M" and "R", have the meanings previously described.

$$nM(OH)_2 + nTi(OR)_4 \rightarrow [MTiO_2(OR)_2]_n + 2nROH$$

EXAMPLE 1

26.5 g (0.155 mol) of $Ba(OH)_2$ as the $M(OH)_2$, 43.2 g (0.152 mol) of $Ti[OCH(CH_3)_2]_4$ as the $Ti(OR)_4$ and 60 mol of para-xylene were charged in a four inlet type of flask having 200 ml of volume capacity, fitted with a refluxing device combined with a cooler, an agitator and a thermometer.

The temperature of the reactants was raised with a simultaneous agitating step in a nitrogen atmosphere and an isopropanol was initially distilled at 120° C. of reaction temperature.

Further, its reaction under a refluxing step of the para-xylene was continuously carried out during two hours and then, the reaction was finished.

In these times, a white muddy solution was changed and discoloured as a light yellowish solution. 17 g (0.297 mol) of the isopropanol was distilled out. After having filtered one part of insoluble $BaCO_3$, the reaction solution was heated under a reduced pressure and the para-xylene was distilled and removed and then, 50.7 g of light yellowish solid material was obtained.

This material was confirmed to have the isopropyl group by procedures of IR and NMR and further, it was identified as a material having a composition formula of $BaTiO_2[OCH(CH_3)_2]_2$ by an elementary analysis value of Ba and Ti.

Further, it was identified as having 2,620 of molecular weight with a measurement for a depression of freezing point of the para-xylene solution and it was assumed as octamer.

Subsequently, various kinds of the composite oxyalkoxides were synthesized by replacing variously the kinds of $M(OH)_2$ and $Ti(OR)_4$ and performing the same procedure.

The synthetic condition and the synthetic results are set forth in Table 1:

$_8[OCH(CH_3)_2]_{0.2}$ as the identification results of the IR and NMR procedures and elementary analysis.

Further, it was assumed to have 1,190 of molecular weight by a measurement for the depression of freezing point of para-xylene solution.

Figure 1:
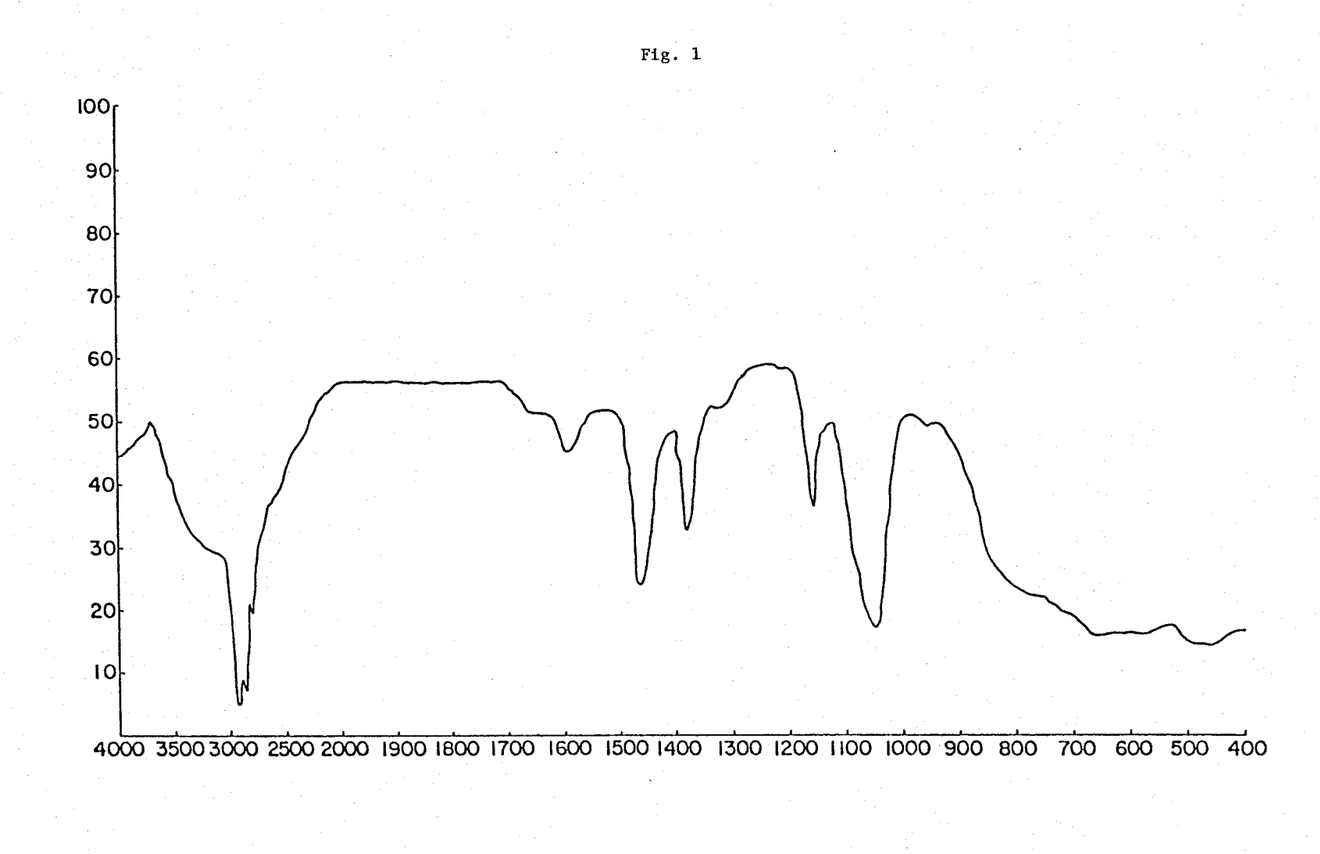

The IR curve of the obtained compound of $BaTiO_2(OCH)_{1.8}[OCH(CH_3)_2]_{0.2}$ is set forth in FIG. 1.

The elementary analysis value: Ba (49.6%); Ti (16.9%); The calculation value: Ba (48.2%); Ti (16.8%).

EXAMPLE 3

6.1 g (0.050 mol) of $Sr(OH)_2$ and 160 g of methanol ($CH_3OH$) were charged in the same apparatus employed in Example 1. Those reactants were heated at 65° C. of temperature with an agitating step and thereby, the methanol ($CH_3OH$) was refluxed.

In continuance of the methanol ($CH_3OH$) refluxing step, a solution consisting of 14.4 g (0.050 mol) of $Ti[OCH(CH_3)_2]_4$ and 35 g of benzene was dropped in the reaction system during 3 hours and thereby, a reaction slurry was obtained.

The solvent was distilled off and removed from it under a reduced pressure and thereby, the reaction compound was obtained.

The reaction compound was identified as a composition of $SrTiO_2(OCH_3)_{1.9}[OCH(CH_3)_2]_{0.1}$ as the identification results of the IR and NMR procedures and by elementary analysis.

It was assumed to have 1,800 of molecular weight and to be an octamer.

Figure 2:
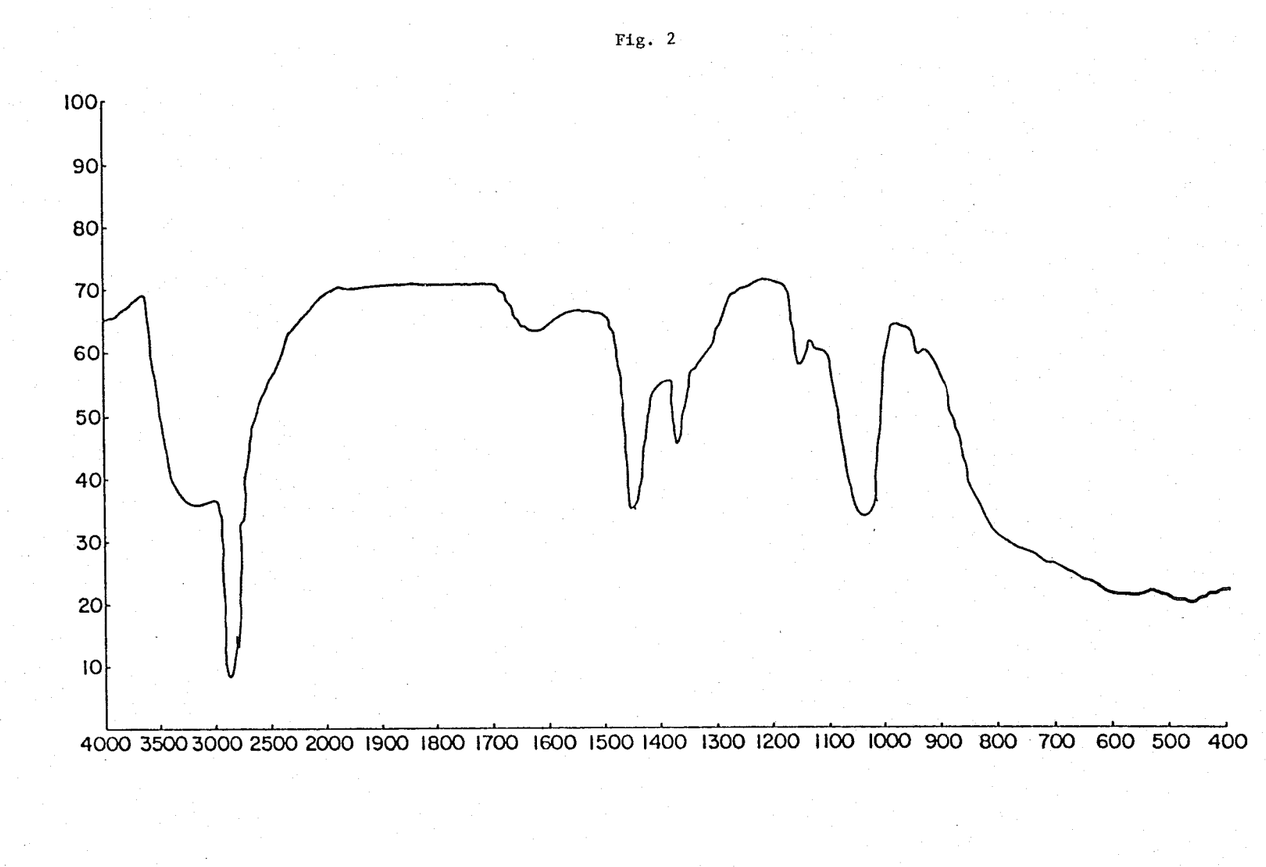

The IR curve of $SrTiO_2(OCH_3)_{1.9}[OCH(CH_3)_2]_{0.1}$ is set forth in FIG. 2.

Elementary analysis value: Sr: 37.2 (%); Ti: 21.0 (%);

TABLE 1

| Reaction formula No. | \multicolumn{6}{c}{$n.M(OH_2) + n.Ti(OR)_4 \rightarrow [MTiO_2(OR)_2]_n + 2nROH$} |
|---|---|---|---|---|---|---|---|
| | M | —OR | Solvent | temperature/time | Molecular Weight | n | Elementary Analysis Analy. Calc. |
| 1-(1) | Ba | $-OCH(CH_3)_2$ | para-xylene | 120° C./2 Hr | 2602 | 8 | Ba: 40.6, 40.9 Ti: 14.5, 14.3 |
| 1-(2) | Sr | $-OCH(CH_3)_2$ | — | 180° C./2 Hr | — | — | Sr: 32.3, 30.7 Ti: 17.6, 16.8 |
| 1-(3) | Ba | $-O(CH_2)_3CH_3$ | Diethyl-benzene | 104° C./2 Hr | — | — | Ba: 36.9, 37.8 Ti: 14.4, 13.2 |
| 1-(4) | Sr | $-O(CH_2)_3CH_3$ | Decalin | 185° C./11 Hr | — | — | Sr: 28.2, 27.9 Ti: 14.9, 15.3 |
| 1-(5) | Ba | $-O(C_6H_{10})-2-C_2H_5$ | — | 215° C./13 Hr | — | — | Ba: 40.9, 40.3 Ti: 14.3, 14.5 |

EXAMPLE 2

A solution consisting of 6.2 g (0.036 mol) of $Ba(OH)_2$ and 50 ml of methanol ($CH_3OH$) was charged in a four inlet type of flask having 200 ml of volume capacity and being fitted with a refluxing cooler, an agitator and a thermometer.

The solution was heated at 80° C. temperature in a nitrogen gas atmosphere and by maintaining the 80° C. above temperature, 9.6 g (0.034 mol) of $Ti[OCH(CH_3)_2]_4$ and 30 ml of isopropanol $[(CH_3)_2CHOH]$ were dropped in the flask.

The isopropanol $[(CH_3)_2CHOH]$ and the methanol $[CH_3OH]$ were distilled off from the homogeneous reaction solution at a temperature of 80° C. or less and a vacuum state and 10.0 g of the reaction compound was obtained.

The reaction compound was identified as a compound having a composition formula: $BaTiO_2(OCH_3)_{1-}$ Calculation value: Sr: 37.7 (%); Ti: 20.6 (%).

EXAMPLE 4

3.4 g (0.01 mol) of $BaTiO_2[OCH(CH_3)_2]_2$ obtained in Example: 1-(1) was dissolved in 20 ml of xylene and by maintaining it in a heating step at 80° C. of temperature, 1.2 g (0.02 mol) of ethylene glycol was dropped in it and thereby a white precipitate was obtained. The white precipitate was filtered and it was dried and thereby, 3.4 g of the composition of $BaTiO_2(OCH_2CH_2OH)_2$ was obtained.

Figure 3:
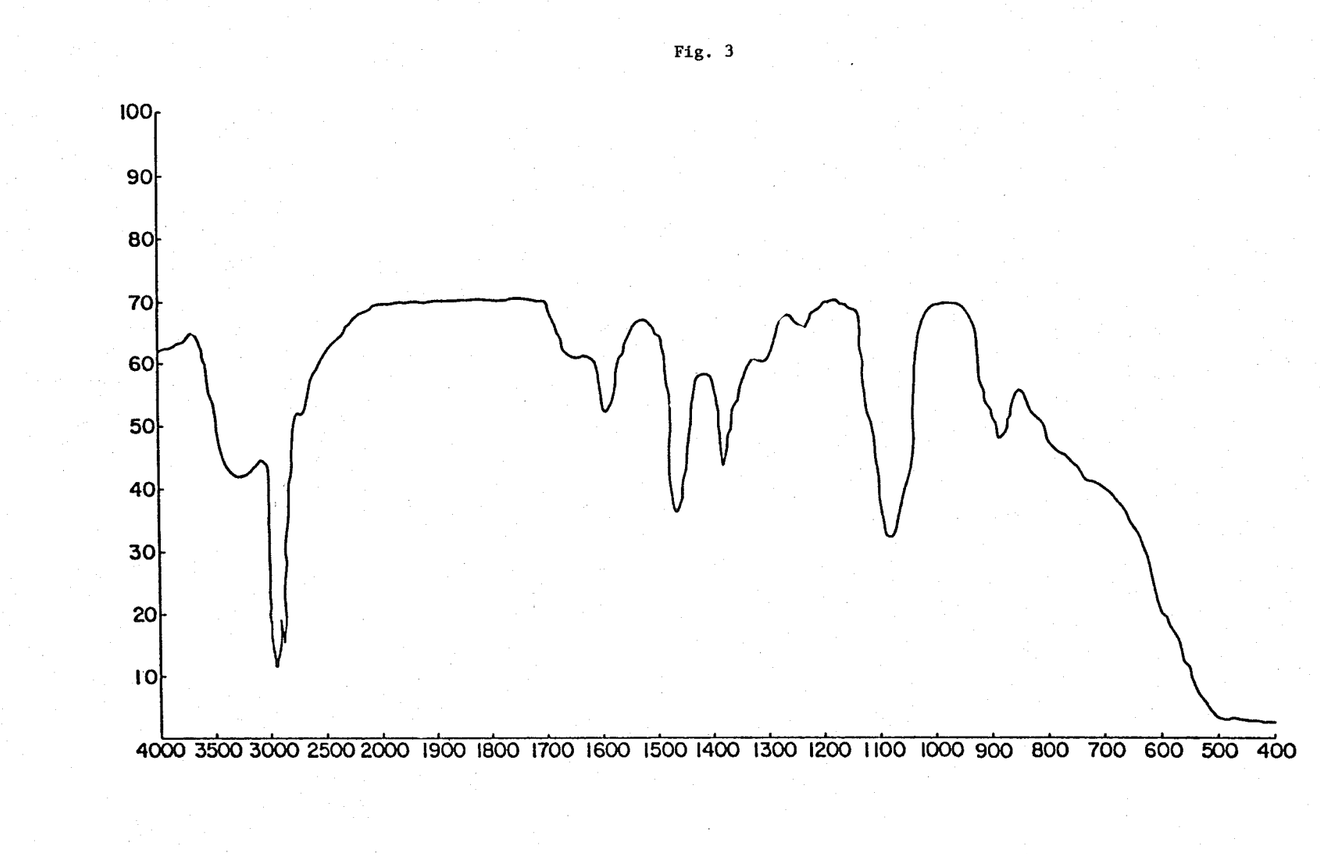

The IR curve of $BaTiO_2(OCH_2CH_2OH)_2$ is set forth in FIG. 3.

The Elementary analysis value: Ba (39.8%); Ti (14.2%); The calculation value: Ba (40.5%; Ti (14.1%).

EXAMPLE 5

3.4 g (0.01 mol) of the $BaTiO_2[OCH(CH_3)_2]_2$ obtained in Example: 1-(1) was dissolved in 20 ml of xylene and by maintaining it in a heating step at 80° C. of temperature, 2.2 g (0.02 mol) of benzyl alcohol was dropped in it and thereby, the homogeneous reaction solution was obtained. By distillating off the xylene from the said reaction solution 4.2 g of a composition of $BaTiO_2(OCH_2 \cdot C_6H_5)_2$ was obtained.

It was assumed to be a tetramer having 1,800 of molecular weight.

The elementary analysis value: Ba (31.3%); Ti (11.3%); The calculation value: Ba (31.8%); Ti (11.1%).

EXAMPLE 6

8.6 g (0.05 mol) of $Ba(OH)$, 28.4 g (0.1 mol) of $Ti[OCH(CH_3)_2]_4$ and 50 ml of decalin was charged in the same apparatus employed for Example 2 and it was heated at 190° C. of temperature and simultaneously agitated and an isopropanol was distilled off with the solvent refluxing step. After having finished the reaction during three hours, a homogeneous reaction solution was obtained. By distilling off the solvent from the said reaction solution under a vacuum state and it was dried and thus, the composition of $Ba_{0.5} \cdot Sr_{0.5} \cdot TiO_2 \cdot [OCH(CH_3)_2]_2$ was obtained.

EXAMPLE 7

3.7 g (0.020 mol) of $Ti[OCH(CH_3)_2]_4$, 3.2 g (0.020 mol) of BaO and 30 ml of methanol were charged in the same apparatus employed in Example 2 and by heating it at 65° C. of temperature with a simultaneous agitating and refluxing step, the reaction was carried out during two hours and thus, a homogeneous reaction solution was obtained.

Figure 4:
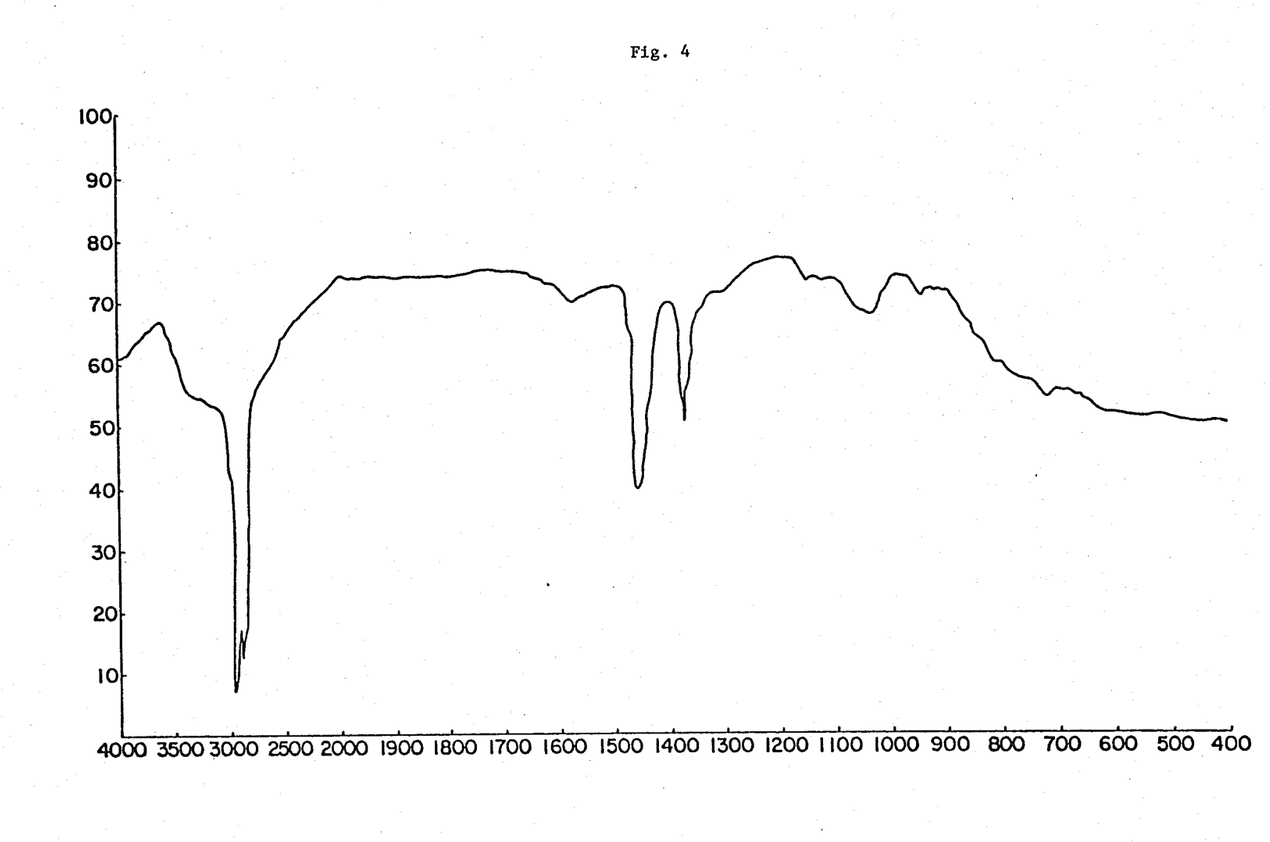

The solvent was distilled off from the said reaction solution and it was dried and the composition of $BaTiO_2(OCH_3)_{1.4}][OCH(CH_3)_2]_{0.6}$ was obtained. The IR curve of a composition: $BaTiO_2(OCH)_{1.4}[OCH(CH_3)_2]_{0.6}$ is set forth in FIG. 4.

The elementary analysis value: Ba (50.9%); Ti (20.1%); The calculation value: Ba (52.6%); Ti (18.3%).

EXAMPLE 8

28.5 g (0.085 mol) of $BaTiO_2[OCH(CH_3)_2]_2$ prepared in Example: 1-(1) and 22.8 g of para-xylene were charged in a four inlet type of flask having 200 ml of volume capacity and being fitted with a refluxing cooler, an agitator and a thermometer. Then, 8.5 g (0.85 mol) of acetylacetone ($CH_3COCH_2COCH_3$) was gradually dropped in reactants at room temperature in a nitrogen gas atmosphere.

In the proceeding of the dropping step, an exothermic phenomenon did occur and a partial precipitation arose in the reaction system. Then, it was heated and, when the reaction temperature reached about 100° C. of temperature, an isopropanol was initially distilled out. Simultaneously, the precipitate was dissolved in it.

4.3 g (0.072 mol) of the isopropanol was distilled out with the heating step during about two hours.

The reaction solution obtained was transparent without causing any sediment, even after it was exposed in the atmosphere during six hours.

The solvent was distilled out from the reaction solution obtained at a temperature of 50° C. or less and under a reduced pressure. 32.1 g of the reaction compound was obtained.

The reaction compound was identified as a compound having a composition formula: $BaTiO_2 \cdot [OCH(CH_3)_2][OCOCH_2COCH_2]_{\frac{1}{2}}$ with the identifying results of the IR and NMR procedures and the elementary analysis.

Further, it was assumed as a dimer having 840 of molecular weight by measuring the depression of the freezing point of the para-xylene solution.

Figure 5:
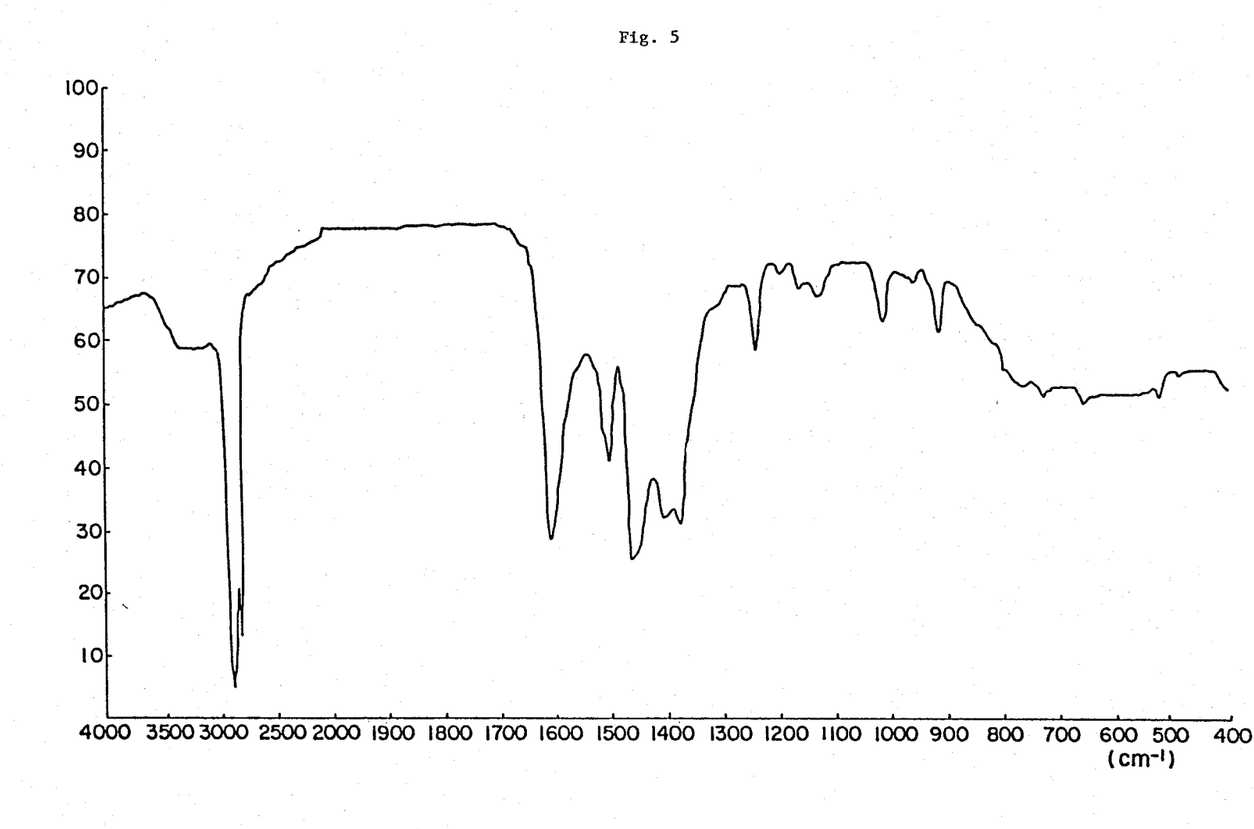

The IR chart for the reaction compound obtained in this Example is set forth in FIG. 5.

The elementary analysis value: Ba (37.2%); Ti (13.4%); The calculation value: Ba (36.6%); Ti (12.8%).

EXAMPLE 9

25.0 g (0.080 mol) of $SrTiO_2[O(CH_2)_3CH_3]$ prepared in the Example: 1-(4) and 50 ml of decalin were charged in the same apparatus employed in the Example 8. 6.0 g (0.040 mol) of triethanolamine was gradually added in it at room temperature and in a nitrogen gas atmosphere.

In the proceeding of the dropping step, an exothermal phenomenon did occur. The temperature was still raised with a heating step and when reaching to about 125° C. of temperature, a normal butanol started to distill out. The normal butanol was distilled out by an amount of 5.7 g (0.077 mol).

The reaction solution was transparent without generating any sediment, even when it was exposed to the atmosphere during 6 hours. A gelled material obtained was heated at a temperature of 90° C. or less and under a reduced pressure and thereby the decalin was distilled out and thus, 25.4 g (0.081 mol) of the reaction compound was obtained.

The reaction compound was identified as the composition formulated by: $SrTiO_2[O(CH_2)_3CH_3] \cdot [(OCH_2CH_2)_2N(CH_2)_2OH]_{\frac{1}{2}}$ by means of the IR and NMR procedures and its elementary analysis. Further, it was assumed as a heptamer having 2,050 of molecular weight by measuring the depression of the freezing point of the para-xylene solution.

The elementary analysis value: Sr (28.4%); Ti (15.2%); The calculation value: Sr (27.9%); Ti (15.3%).

EXAMPLE 10

14.5 g (0.043 mol) of the $BaTiO_2[OCH(CH_3)_2]_2$ prepared in the Example: 1-(1), 11.6 g of para-xylene, 12.3 g (0.043 mol) of $SrTiO_2[OCH(CH_3)_2]_2$ prepared with the same process in the Example: 1-(2) and 24.5 g of decalin were charged in the same apparatus employed in the Example 8. 7.7 g (0.086 mol) of lactic acid was dropped in reactants with a simultaneous agitating step. The reaction system being accompanied with an exothermal phenomenon was initiated to separate a white precipitate. By keeping the same condition, it was heated at a temperature of 98° C. or less and then, its temperature was raised and thereby, isopropanol was distilled out. The distilled isopropanol was an amount of 9.6 g (0.16 mol).

The reaction solution obtained was transparent without separating any sediment, even when it was exposed to the atmosphere during 6 hours. The white precipitate separated was filtered and the filtrate was washed with 50 ml of para-xylene and it was dried and thus, 24.5 g of the reaction compound was obtained.

The reaction compound was identified as a compound having a composition formula: $Ba_{0.5}Sr_{0.5}TiO_2 \cdot [OCH(CH_2)COO]$ with the measurements of the IR and NMR procedure (i.e. the measurement by decomposing the white powders in a system of concentrated DCl-$D_2O$) and the elementary analysis.

Figure 6:
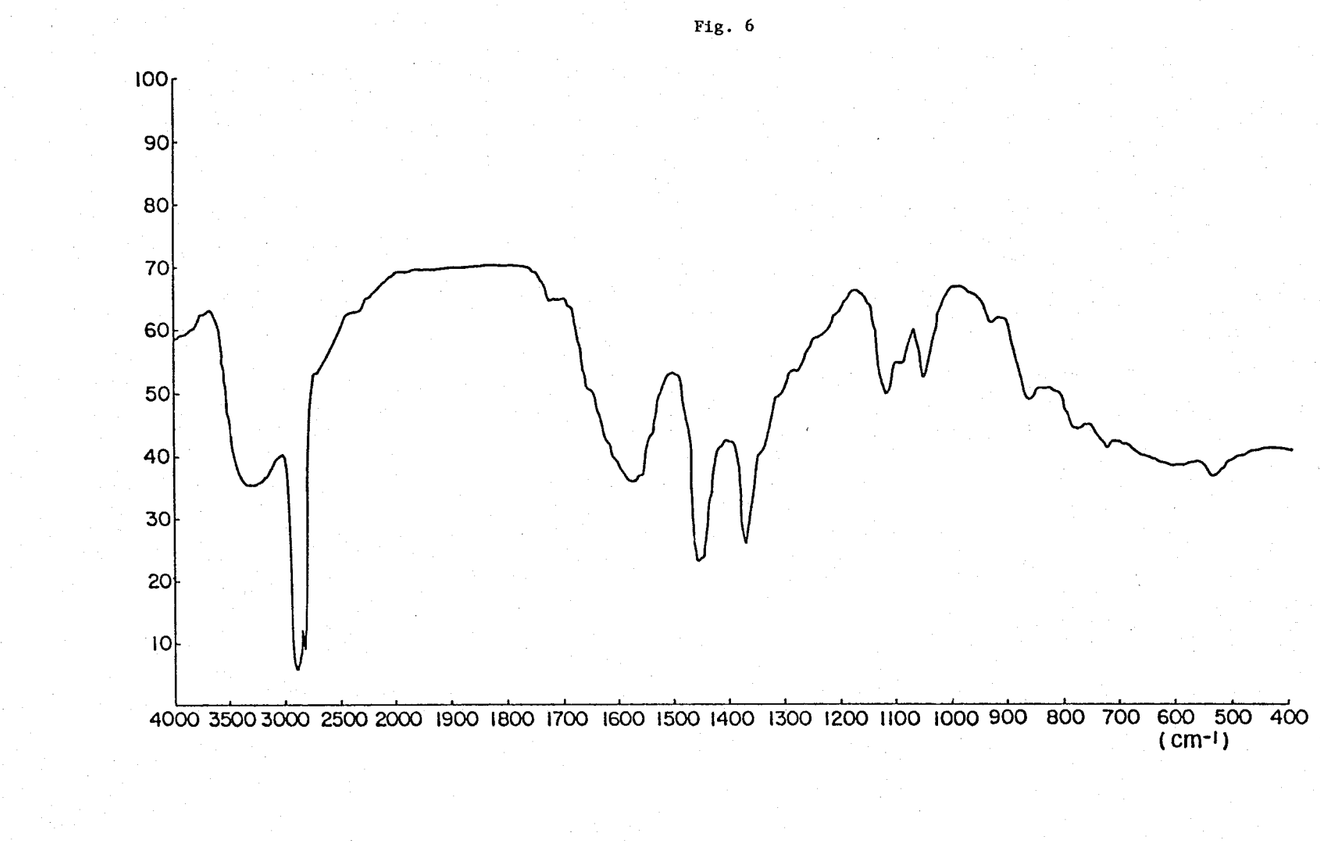

The IR chart for the reaction compound is set forth in FIG. 6.

The elementary analysis value: Sr (28.4%); The calculation value: Sr (27.9%).

REFERENCE EXAMPLE

A stability test for the stability of the composite oxyalkoxide obtained in Examples 1-(1) and 1-(4) as compared with the stability of the composite oxyalkoxide derivatives obtained in the Examples 8 to 10 was carried out. This comparison results are set forth in Table 2.

TABLE 2

| | Stability of the solid |
|---|---|
| Example 8 | Even if exposed in the atmosphere during one day, its weight was not decreased and any change did not appear in the IR chart. |
| Example 9 | Even if exposed in the atmosphere during one day, its weight was not decreased and any change did not appear in the IR chart. |
| Example 10 | After being exposed in the atmosphere, its weight was not decreased. |
| Example 1-(1) | After being exposed in the atmosphere, its weight was not decreased and the absorption of TiO—iPr in the IR chart was decreased. |
| Example 1-(4) | After being in the atmosphere during one day, its weight was not decreased and the absorption of TiO—nBu in the IR chart was decreased. |

APPLIED EXAMPLE 1

10 g (0.0298 mol, as a converted rate to the monomer) of the compound of $BaTiO_2[OCH(CH_3)_2]_2$ synthesized in the Example: 1-(1) was dissolved in about 100 ml of para-Xylene and it was heated at a temperature of 90° C. to 100° C. 1.07 g (0.060 mol) of water was gradually dropped in the reactants under heated condition by using a micro-syringe. In the course of two hours, the precipitate produced was filtered and the filtrate was washed with water and it was dried at 100° C. of temperature under a reduced pressure and thus, 6.9 g of the compound of $BaTiO_3$ with 99.3 percent of yield rate. The $BaTiO_3$ was identified as a cubic Crystal (a=4.051) with X ray diffraction meter.

Further, it was observed as a coagulated material having a diameter of 1 to 2 micron which consists of coagulated fine particles having a granular diameter of 0.1 micron or less by using a scanning electronical microscope.

APPLIED EXAMPLE 2

5 g (0.0149 mol) of the $BaTiO_2[OCH(CH_3)_2]_2$ synthesized in the Example: 1-(1) was calcined at 900° C. of temperature during two hours under the air ventilation, whereby 3.5 g (0.0149 mol) of $BaTiO_3$ powders was obtained. This material was identified as a cubic crystal (a=4.0 b=26 and c=4,000) with X ray diffraction. Further, by using the scanning electrical microscope, it was observed as coagulated material having a diameter of 1 to 2 micron which consists of the fine particles having 0.2 micron of granular diameter.

APPLIED EXAMPLE 3

5.9 g (0.018 mol) of the $BaTiO_2[OCH(CH_3)_2]_2$ synthesized in the Example 1-(1) was dissolved in 40.1 g of normal butanol and thereby, the adjusted solution containing 8.9 weight percent of the converted $BaTiO_3$. A silica glass plate having a size of width (30 mm)×length (50 mm)×thickness (3 mm) was immersed in the adjusted solution during one minute in a nitrogen atmosphere and the silica glass plate was lifted with a constant velocity of 3 cm/minute. Its solvent was blown off from the silica glass plate in the presence of nitrogen gas and then, it was dried at 100° C. of temperature for one hour in the air and subsequently, it was baked at 700° C. of temperature during 3 hours in an electric furnace. Thus, a semi-transparent film of $BaTiO_3$ was obtained.

APPLIED EXAMPLE 4

5 g (0.0175 mol) of the $SrTiO_3[OCH(CH_3)_2]_2$ obtained in the Example 1-(2) was calcined at 900° C. of temperature during two hours under an air ventilation, whereby 3.1 g (0.0169 mol) of the $SrTiO_3$ powders was obtained.

It was identified as $SrTiO_3$ having the cubic crystal with X ray diffraction method (a=3.884). Further, it was observed as the coagulated material of 1 to 2 micron grains consisting of fine particles having 0.1 micron of granular diameter by using the scanning electron microscope.

APPLIED EXAMPLE 5

The one part of the homogeneous solution obtained in the Example 1-(3) was sampled in a petri dish and it was exposed to the air and thereby it was changed to a transparent gelled compounds. It was dried with irradiation of infrared ray lamp, whereby it was decomposed as the fine particles. It was subjected to an IR process and elementary analysis shows that the fine particles correspond to the powders of $BaTiO_2CO_3$.

The fine particles were baked at 700° C. of temperature during two hours and the fine particles of $BaTiO_3$ having a cubic crystal was obtained.

It was a coagulated material having a size of 1 to 2 micron which consists of the fine particles having a granular diameter of 0.1 micron or less.

APPLIED EXAMPLE 6

15.5 g (0.043 mol) of the powders obtained in the Example 8 was dissolved in 370 g of normal butanol and the solution was adjusted as a solution containing 5 weight percent of converted concentration of $BaTiO_3$. The adjusted solution was stable, even when exposed to air so that a quartz glass plate having a size of width (30 mm)×length (50 mm)×thickness (3 mm) was immersed in the adjusted solution in the presence of air. In the course of one minute, the quartz glass plate was lifted up with a constant velocity of 40 cm/minute.

It was air-dried during 10 minutes and further, it was dried at 100° C. temperature during one hour and then, it was baked at 1,100° C. of temperature during 3 hours in an electric furnace, whereby a transparent film of $BaTiO_3$ was obtained.

APPLIED EXAMPLE 7

The composite oxyalkoxides and the composite oxyalkoxide derivatives obtained in the Examples 2 to 10 were hydrolyzed or thermally decomposed and thereby the salts of alkaline earth metal titanate were obtained. The results are set forth in Table 3.

TABLE 3

| Example No. | Decomposition process | The reaction compound | | |
| | | Composition formula* | External appearance* | Granular diameter** |
|---|---|---|---|---|
| 2 | Hydrolysis | $BaTiO_3$ | crystal | 0.1 micron or less |
| 3 | Thermal decomposition | $SrTiO_3$ | crystal | 0.1 micron or less |
| 4 | Thermal decomposition | $BaTiO_3$ | crystal | 0.1 micron or less |
| 5 | Hydrolysis | $BaTiO_3$ | crystal | 0.1 micron or less |

TABLE 3-continued

| Example No. | Decomposition process | Composition formula* | External appearance* | Granular diameter** |
|---|---|---|---|---|
| 6 | Thermal decompsoition | $Ba_{0.5}Sr_{0.5}.TiO_3$ | crystal | 0.1 micron or less |
| 7 | Hydrolysis | $BaTiO_3$ | crystal | 0.1 micron or less |
| 8 | Thermal decomposition | $BaTiO_3$ | crystal | 0.1 micron or less |
| 9 | Thermal decomposition | $SrTiO_3$ | crystal | 0.1 micron or less |
| 10 | Thermal decomposition | $Ba_{0.5}Sr_{0.5}.TiO_3$ | crystal | 0.1 micron or less |

Note
*By the X ray diffraction method
**By the scanning electronical microscope

FEASIBILITY OF INDUSTRIAL UTILIZATION

The composite oxyalkoxides and its derivatives by the present invention are a novel useful, organo-metal compound for producing the titanate salts of alkaline earth metal by the solution method and these compounds and their derivatives have the following features.

(1) The composite oxyalkoxides and their derivatives are able to produce easily the titanate salts of alkaline earth metal by means of a hydrolysis or a thermal decomposition under appropriate condition.

(2) The composite oxyalkoxides and their derivatives have solubility in organic solvents and consequently, by adding a moulding agent, a moulded product, such a film, a plate or a fiber can be produced. Further, said mouldings or a non-moulded material is treated with a hydrolysis step or a thermally decomposing step and thereby, the titanate salts of alkaline earth metal in a fine particle form, a film form, a plate form or a fibrous form as a desirable form can be obtained.

(3) The composite oxyalkoxides and their derivatives have the solubility in organic solvent, so that by preliminary using a sifter, a depressor, a semiconductively denaturing agent or a sintering aid in the titanate salt(s) of alkaline earth metal, a homogeneous mixture is obtained.

(4) The composite oxyalkoxides and their derivatives have a ratio of Ti/M as a stoichiometric value, so that the ratio of Ti/M in the titanate salt(s) of alkaline earth metal obtained with the hydrolysis or the thermal decomposition is a stoichiometric value or its extremely approximate value.

(5) By using the raw material, obtained easily with a comparatively low cost, a simple manufacturing process can be carried out.

(6) The composite oxyalkoxide derivative have a more superior storage stability in comparison with the composite oxyalkoxides.

The present invention is to provide the composite oxyalkoxides and their derivative as a novel material which are useful for manufacturing titanate salt(s) of alkaline earth metal and its industrial significance is very great.

What is claimed is:

1. A composite oxyalkoxide represented by a composition formula [I] as the formula of a repeating constituent unit as follows:

$$[MTiO_2(OR)_2] \quad [I]$$

said material consisting of monomers having a repeating constituent unit or oligomers thereof having a repeating constituent unit, the repetition being in the range of from 2 to 20, said repeating units being selected from the group consisting of
$BaTiO_2[OCH(CH_3)_2]_2$, $SrTiO_2[OCH(CH_3)_2]_2$, $BaTiO_2[O(CH_2)_3CH_3]_2$,
$SrTiO_2[O(CH_2)_3CH_3]_2$, $BaTiO_2[O(C_6H_{1\text{-}0})\text{---}2\text{---}C_2H_5]_2$, $BaTiO_2(OCH_2.C_6H_5)_2$,
$BaTiO_2(OCH_2.CH_2OH)_2$,
$BaTiO_2(OCH_3)_a[OCH(CH_3)_2]_b$ where $a+b=2$,
$SrTiO_2(OCH_3)_a[OCH(CH_3)_2]_b$ where $a+b=2$ and
$Ba_xSr_yTiO_2[O(CH_2)_3CH_3]_2$ where $x+y=1$,
and R denotes a material selected from the group consisting of a straight or branched chain alkyl radical having 1 to 6 carbon atoms, an alkyl radical substituted by a hydroxy group, an alkoxy group having 1 to 3 carbon atoms or chlorine, a substituted or unsubstituted cycloalkyl group, an alkenyl group, and an aralkyl group.

2. A material according to claim 1 wherein the composite oxyalkoxide is synthesized by reacting an alkoxy titanium having the general formula [II]:

$$Ti(OR)_4 \quad [II]$$

with an alkaline earth metal hydroxide having the general formula [III]:

$$M(OH)_2 \quad [III]$$

wherein R has the same meaning as set forth in claim 1.

3. A material according to claim 1 wherein the composite oxyalkoxide is synthesized by a reaction of a lower alkoxy titanium and an alkaline earth metal hydroxide and further making said composite oxyalkoxide to react with an alcohol having an (—OR) group, where R has the meaning set forth in claim 1.

4. A material as claimed in claim 3 wherein the lower alkoxy titanium is tetraisopropoxy titanium or tetrabutoxy titanium or mixtures thereof.

5. A material as claimed in claim 3 wherein the reaction condition is a reaction time of about 1 to about 3 hours at a refluxing temperature in the presence of a non-polar organic solvent.

6. A material as claimed in claim 1 wherein the (OR) group is partially or totally substituted with a chelating agent.

7. A material according to claim 6 wherein the chelating agent is selected from the group consisting of β-diketones, α- or β-ketonic acids, α- or β-ketonic acid esters, α- or β-oxy-acids, α- or β-oxy-acid esters, α- or β-oxy-ketones, α- or β-oxy-aldehydes, α-amino acids, or α- or β-amino alcohols.

8. A material according to claim 7 wherein the composite oxyalkoxide which is partially or totally substituted with a chelating agent is obtained by a reaction of the composite oxyalkoxide with the chelating agent for a reaction time of 1 to 50 hours at a refluxing temperature using a non-polar organic solvent.

* * * * *